US010368961B2

(12) United States Patent
Paehl et al.

(10) Patent No.: US 10,368,961 B2
(45) Date of Patent: Aug. 6, 2019

(54) METHOD OF MAKING A TRANSFER TRAY

(71) Applicant: 3M INNOVATIVE PROPERTIES COMPANY, St. Paul, MN (US)

(72) Inventors: Ralf M. Paehl, Melle (DE); Dietmar Blees, Lohne (DE)

(73) Assignee: 3M Innovative Properties Company, St. Paul, MN (US)

( * ) Notice: Subject to any disclaimer, the term of this patent is extended or adjusted under 35 U.S.C. 154(b) by 255 days.

(21) Appl. No.: 15/105,484

(22) PCT Filed: Dec. 10, 2014

(86) PCT No.: PCT/US2014/069465
§ 371 (c)(1),
(2) Date: Jun. 16, 2016

(87) PCT Pub. No.: WO2015/094842
PCT Pub. Date: Jun. 25, 2015

(65) Prior Publication Data
US 2016/0310239 A1 Oct. 27, 2016

(30) Foreign Application Priority Data
Dec. 18, 2013 (EP) ..................................... 13198181

(51) Int. Cl.
*A61C 7/14* (2006.01)
*A61C 7/00* (2006.01)
(Continued)

(52) U.S. Cl.
CPC .............. *A61C 7/146* (2013.01); *A61C 7/002* (2013.01); *B29C 41/14* (2013.01);
(Continued)

(58) Field of Classification Search
CPC .......... A61C 7/146; A61C 7/002; B29C 41/14
See application file for complete search history.

(56) References Cited

U.S. PATENT DOCUMENTS 7,020,963 B2   4/2006   Cleary
7,210,929 B2   5/2007   Raby
(Continued)

FOREIGN PATENT DOCUMENTS

EP    2604218       6/2013
JP    2001190569    7/2001
(Continued)

OTHER PUBLICATIONS

International Search Report for PCT International Application No. PCT/US2014/069465, dated Mar. 9, 2015, 6 pages.

*Primary Examiner* — Jacob T Minskey
*Assistant Examiner* — Melody Tsui

(57) ABSTRACT

A method of making a transfer tray includes providing a physical mockup having a shape that corresponds to a positive shape of a patient's dental arch and a positive shape of one or more bracket analogs. A transfer tray may be formed over the physical mockup, with the transfer tray representing a negative replica of at least a portion of the mockup. One or more receptacles are accordingly formed in the ray, each receptacle approximating a least a portion of the shape of a bracket analog. A bracket associated with a bracket analog is placed into a receptacle of the one or more receptacles and a filler material is introduced into at least one receptacle.

10 Claims, 8 Drawing Sheets

(51) Int. Cl.
  *B29C 41/14* (2006.01)
  *B29C 45/14* (2006.01)
  *B29C 51/10* (2006.01)
  *B29C 65/70* (2006.01)
  *B29C 64/00* (2017.01)
  *B29C 64/40* (2017.01)
  *A61C 13/00* (2006.01)
  *B29K 67/00* (2006.01)
  *B29K 69/00* (2006.01)
  *B29K 83/00* (2006.01)
  *B29K 91/00* (2006.01)
  *B29L 31/00* (2006.01)

(52) U.S. Cl.
  CPC ........ *B29C 45/14467* (2013.01); *B29C 51/10* (2013.01); *B29C 64/00* (2017.08); *B29C 64/40* (2017.08); *B29C 65/70* (2013.01); *A61C 13/0013* (2013.01); *B29K 2067/00* (2013.01); *B29K 2069/00* (2013.01); *B29K 2083/00* (2013.01); *B29K 2091/00* (2013.01); *B29L 2031/753* (2013.01)

(56) References Cited

U.S. PATENT DOCUMENTS

| | | | |
|---|---|---|---|
| 7,762,815 B2 | 7/2010 | Cinader, Jr. | |
| 7,811,087 B2 | 10/2010 | Wiechmann | |
| 7,845,938 B2 | 12/2010 | Kim | |
| 7,993,133 B2 | 8/2011 | Cinader, Jr. | |
| 8,235,717 B2 | 8/2012 | Kuperman | |
| 2003/0163291 A1* | 8/2003 | Jordan | A61C 7/00 703/1 |
| 2004/0219471 A1* | 11/2004 | Cleary | A61C 7/146 433/3 |
| 2006/0223021 A1 | 10/2006 | Cinader, Jr. | |
| 2010/0279243 A1 | 11/2010 | Cinader, Jr. | |
| 2011/0091832 A1 | 4/2011 | Kim | |

FOREIGN PATENT DOCUMENTS

| | | |
|---|---|---|
| WO | WO 2007-143339 | 12/2007 |
| WO | WO 2010-070710 | 6/2010 |
| WO | WO 2012-136247 | 10/2012 |
| WO | WO 2014-093084 | 6/2014 |

\* cited by examiner

METHOD OF MAKING A TRANSFER TRAY

CROSS REFERENCE TO RELATED APPLICATIONS

This application is a national stage filing under 35 U.S.C. 371 of PCT/US2014/069465, filed Dec. 10, 2014, which claims the benefit of European Application No. 13198181.3, filed Dec. 18, 2013, the disclosure of which is incorporated by reference in its/their entirety herein.

BACKGROUND ART

Orthodontic brackets are used in orthodontic treatments for moving one or more teeth from an initial position (sometimes referred to as malposition or malocclusion) to a desired position in a patient's dentition. For example by an orthodontic treatment the patient's teeth may be moved such that their labial sides are aligned with each other to achieve or maximize an aesthetically pleasant appearance of the overall dentition. Further in some cases one or more teeth may be moved to correct a malocclusion. The movement of teeth is typically achieved by a pre-biased elastic archwire which is attached via brackets to the teeth, and which applies a force to the teeth toward the desired position over a longer time period. The ends of orthodontic archwires are often connected to small appliances known as buccal tubes that are, in turn, secured to the patient's molar teeth. In many instances, a set of brackets, buccal tubes and an archwire is provided for each of the upper and lower dental arches.

In many types of orthodontic techniques, the precise position of the appliances on the teeth is an important factor for helping to ensure that the teeth move to their intended final positions. For example, one common type of orthodontic treatment technique is known as the "straight-wire" technique, where the archwire lies in a horizontal plane at the conclusion of treatment. If, for example, a bracket is attached to the tooth at a location that is too close to the occlusal or outer tip of the tooth, the orthodontist using a straight-wire technique will likely find that the tooth in its final position is unduly intruded. On the other hand, if the bracket is attached to the tooth at a location closer to the gingiva than is appropriate, it is likely that the final position of the tooth will be more extruded than desired.

So-called treatment planning systems have been used to determine the desired position of the teeth in a computer simulation in advance of any actual treatment. Such a planning system helps for example for avoiding collisions between the teeth and brackets in tooth positions outside the initial position, and further allows for the brackets and the archwire to be designed and arranged to match with a variety of clinical situations, for example with the position of the teeth in the initial position, in the desired position, and positions between. In particular for lingual brackets such treatment planning is widely used. Lingual brackets often have a customized design individually for every tooth and patient because, other than the labial surfaces of a tooth, the lingual surfaces greatly vary in shape relative to each other so that a "one size fits all" bracket shape typically cannot be used. Some treatment planning systems also allow for designing such customized brackets which precisely match a tooth surface and the required clinical situations of a patient. Accordingly customized brackets typically have to be precisely placed at positions on the teeth which are predetermined during the treatment planning. For facilitating a precise placement of the brackets on a patient's teeth and for the orthodontist's reference, the brackets are often provided prepositioned on a plaster model replicating the patient's teeth.

Such a plaster model on which the brackets are placed is sometimes used in orthodontics to make a so-called transfer tray for facilitating the placement of the bracket on a patient's teeth. A transfer tray typically is adapted to hold a complete set of brackets at the predetermined position and allow the brackets to be placed and bonded on the teeth in one step.

In general, indirect bonding techniques have involved the use of a transfer tray having a shape that matches the configuration of at least part of a patient's dental arch. A set of appliances such as brackets are releasably connected to the tray at certain, predetermined locations. Adhesive is applied to the base of each appliance, and the tray is then placed over the patient's teeth until such time as the adhesive hardens. Next, the tray is detached from the teeth as well as from the appliances, with the result that all of the appliances previously connected to the tray are now bonded to the respective teeth at their intended, predetermined locations.

For example, as disclosed in WO 01/80761, treatment planning software virtually superimposes brackets on teeth to generate a three-dimensional model comprising the three-dimensional tooth objects plus the virtual brackets at their intended locations. This three-dimensional model is supplied to a stereo lithography (SLA) instrument for manufacturing a plastic model of the teeth with the brackets superimposed thereon. A thermoplastic foil is placed above the SLA model and the model and foil are placed within a pressure chamber. The chamber is pressurized so that the foil envelops the dentition and the brackets. The foil thus obtains small indentations where the brackets can be located.

EP Application No. 1 2196 586 describes a method of making a transfer tray from an integrated physical mockup. The integrated physical mockup represents a shape composed of the positive shape of a patient's dental arch and the positive shape of a set of bracket analogs. The bracket analogs may substantially correspond in shape to the shape of the desired orthodontic bracket, but may include less substantial or fewer undercuts, grooves, and recesses than said corresponding bracket body. The shape of the dental arch and the set of analogs can cooperate to form one contiguous piece, which can allow for creation of a transfer tray in which brackets can be removably placed and positioned without substantially damaging the transfer tray. Further a transfer tray prepared by use of the integrated physical mock up can allow precise positioning of the brackets, while permitting removal of the brackets at relatively low forces.

SUMMARY OF THE INVENTION

Formation of a transfer tray over analogs or approximations of the selected bracket shape puts the method of EP Application No. 1 2196 586 in contrast to many indirect bonding systems, which are typically directly formed over the selected orthodontic bracket or exact approximations thereof. As depicted in FIG. 1, such methods of creating a transfer tray result in spaces corresponding to certain brackets features (e.g., archwire slot, hooks, tiewings, etc.) that are vacant, lest the tray material interfere with the precise placement of the bracket 3 within the receptacle. A tray 1 that has been formed over a bracket analog includes a receptacle 2 that features surfaces conforming to at least a portion of the exterior shape of the corresponding physical bracket 3, but not certain undercuts or recesses of said bracket 4. Accordingly, the selected bracket 3 and transfer tray 1 cooperate, once the bracket 3 is placed in the receptacle 2, to form unfilled voids 4 (i.e., cavities) defined by the receptacle 2 and the bracket features 3a, 3b, 3c.

Pressures generated on the bracket during bonding to a patient's tooth surface may cause excess adhesive on the bonding base (otherwise known in the art as "flash") to exude out from the base and cascade over portions of the bracket body. As depicted in FIG. 2, this excess adhesive can flow into or otherwise fill the space defined by critical bracket features (e.g., hooks, undercuts, and archwire slots) and/or the tray receptacle. The adhesive, designed to bond the bracket base to tooth structure, typically demonstrates an affinity for bracket surfaces and is difficult to remove once engaged. In certain circumstances, adhesive filled or covered areas of the bracket body may render the bracket clinically deficient. For example, an excess of adhesive disposed in an archwire slot may prevent an archwire for being properly seated within the slot, affecting the course of orthodontic treatment. As another example, excess adhesive about a bracket hook or tie wing may impede ligation of the archwire. What is needed, then, is a solution that reduces or eliminates the compelling problems of flash without deleterious affecting the precision placement of the affected bracket or the ease of removal.

The disclosure in one aspect is directed to a method of reducing or eliminating the overflow of excess adhesive ("flash") into critical spaces on orthodontic brackets when such brackets are placed on a tooth surface. The method is well suited for use with transfer trays (often called indirect bonding trays) having one or more receptacles for retaining a bracket, particularly those created over physical models of bracket analogs. A volume constant filler material can be introduced into the receptacle subsequent to formation of the transfer tray, and potentially, placement of the bracket(s) within the receptacle(s). In certain implementations, the volume constant filler may be introduced via channel formed in the tray body. In other implementations, the volume constant filler may be coupled to a physical bracket before placement in transfer tray receptacle. In any event, the filler material is capable of populating the voids and other vulnerable spaces created by the bracket and receptacle.

Introduction of a filler material thus serves to protect the vulnerable bracket features from excess adhesive overflow. Since the filler material can be introduced after transfer tray formation, it can also have minimal effect on the removability of the bracket from the tray. Furthermore, the use of a separate filler material can provide an easily removed portion of the receptacle, enabling the tray to be re-used if desired.

In one aspect, the present disclosure provides a method of making a transfer tray, comprising the steps of:

providing a physical mockup having a shape that corresponds to a positive shape of a patient's dental arch and a positive shape of one or more bracket analogs. A transfer tray is then formed over the physical mockup, the transfer tray comprising a negative replica of at least a portion of the mockup. Forming the transfer tray creates one or more receptacles, with each receptacle featuring a least a portion of the shape of a bracket analog. The method further includes placing a bracket associated with a bracket analog into a receptacle of the one or more receptacles and introducing a filler material into at least one receptacle.

The transfer tray may be formed by providing an elastic sheeting on the physical mockup to cover at least part of the tooth side of the mockup by the sheeting. Next, a plastic sheeting may be disposed on the mockup with the elastic sheeting arranged between the plastic sheeting and the mockup. The plastic sheeting is deformed over the mockup such that it encloses at least the tooth side of the mockup and such that it embraces the elastic sheeting between the plastic sheeting and the mockup. Subsequently, the elastic sheeting is replaced with a hardenable material, which is allowed to harden.

In providing the physical mockup, the disclosure can include the steps of providing a virtual dental arch replicating at least part of a patient's dental arch and providing a virtual set of orthodontic brackets for the virtual dental arch. A virtual set of analogs are accordingly provided (e.g., created), each analog being associated with a virtual bracket of the virtual set of brackets and approximating or representing the shape of the associated virtual bracket. The shape of at least one of the analogs usually differs from the shape of the associated bracket. A virtual mockup is achieved, with the virtual dental arch and the set of virtual analogs merged. A physical mockup can then be manufactured based on the virtual mockup.

In certain aspects, the shape of each analog approximates or represents the shape of the associated bracket; and wherein at least one of the analogs has a different shape than the associated bracket. In similar aspects, the bracket analog includes less substantial or fewer undercuts or recesses than the associated bracket body. Typically, a receptacle and the associated bracket then define one or more voids when the associated bracket is placed in the receptacle, and the filler material accordingly fills at least one void.

In certain aspects the filler material comprises a hardenable material that is allowed to harden proximate the receptacle. Typically, filler material is introduced simultaneously with or after the associated bracket has been placed in the receptacle. In some implementations, the filler material is selected from the group consisting of silicone, wax, and foam. If the filler is sufficiently followable, the filler material may be introduced into the receptacle via a channel formed in the tray.

In another aspect of the present disclosure, a method of controlling excess adhesive during bonding is set forth. Such flash controlling methods include the steps of providing a transfer tray having a receptacle with a configuration matching at least a portion of an associated orthodontic bracket placing an associated bracket into a receptacle; and introducing a volume constant filler into the receptacle, wherein the filler is introduced simultaneously with or after placement of the bracket.

In certain aspects, the bracket and the receptacle cooperate to define voids, and the filler is introduced into the voids. The filler may be introduced into the receptacle via a channel formed in the tray. The receptacle may include a release agent applied before or after the placement of an associated bracket.

For the purpose of this specification the term "virtual" refers to a three-dimensional computer representation of an object, preferably based on a mathematical representation of a three-dimensional shape in data form and processable by a computer. Such virtual objects in the form of data including their visualizations (for example wire frames or digital renderings) are widely known in the field of Computer Aided Design (CAD).

For the purpose of the present specification the term "set of" refers to a "plurality of".

As used herein, "hardenable" is descriptive of a material or composition that can be cured (e.g., polymerized or crosslinked) or at least partially solidified, for example, by removing solvent (e.g., by evaporation and/or heating);

heating to induce polymerization and/or crosslinking; irradiating to induce polymerization and/or crosslinking; and/or by mixing one or more components to induce polymerization and/or crosslinking.

As used herein, "hardened" refers to a material or composition that has been cured (e.g., polymerized or crosslinked) or solidified.

As used herein, the terms "volume constant material" and "volume constant filler" refer to hardenable materials that experience a volume reduction of no more than 85% upon hardening.

"Mesial" means in a direction toward the center of the patient's curved dental arch.

"Distal" means in a direction away from the center of the patient's curved dental arch.

"Occlusal" means in a direction toward the outer tips of the patient's teeth.

"Gingival" means in a direction toward the patient's gums or gingiva.

"Facial" means in a direction toward the patient's cheeks or lips.

"Lingual" means in a direction toward the patient's tongue.

In several places throughout the application, guidance is provided through lists of examples, which examples can be used in various combinations. In each instance, the recited list serves only as a representative group and should not be interpreted as an exhaustive list.

Layers in the depicted embodiments are for illustrative purposes only and are not intended to define the thickness, relative or otherwise, or the location of any component.

While the above-identified figures set forth several embodiments of the disclosure, other embodiments are also contemplated, as noted in the description. In all cases, this disclosure presents the invention by way of representation and not limitation. It should be understood that numerous other modifications and embodiments can be devised by those skilled in the art, which fall within the scope and spirit of the principles of the invention.

DETAILED DESCRIPTION OF THE ILLUSTRATIVE EMBODIMENTS

Figure 1:
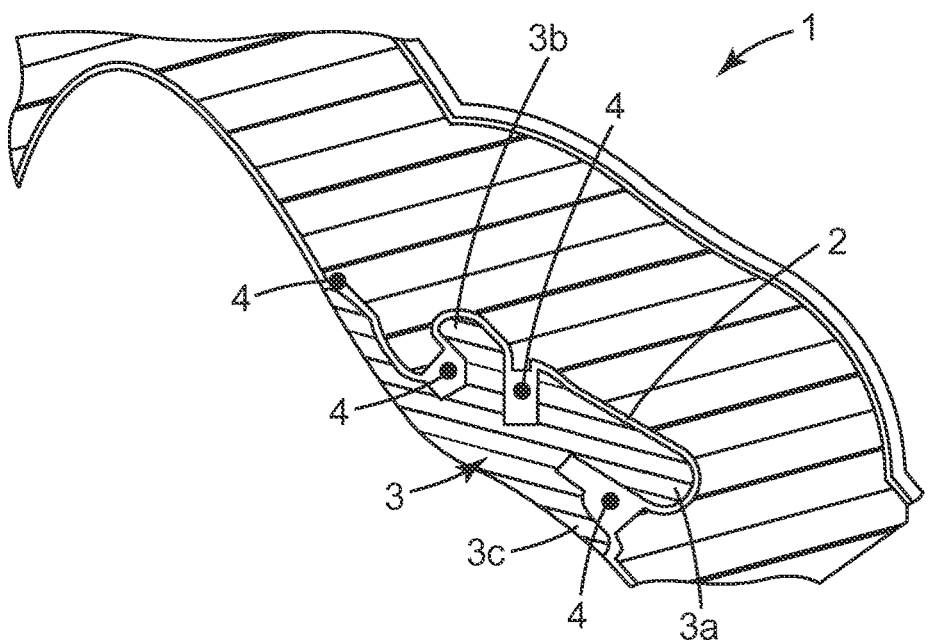
FIG. 1 is a schematic cross-sectional view of a transfer tray having a bracket received in a receptacle.
Figure 2:
FIG. 2 is a depiction of excess adhesive obscuring critical features of an orthodontic bracket.
Figure 3:
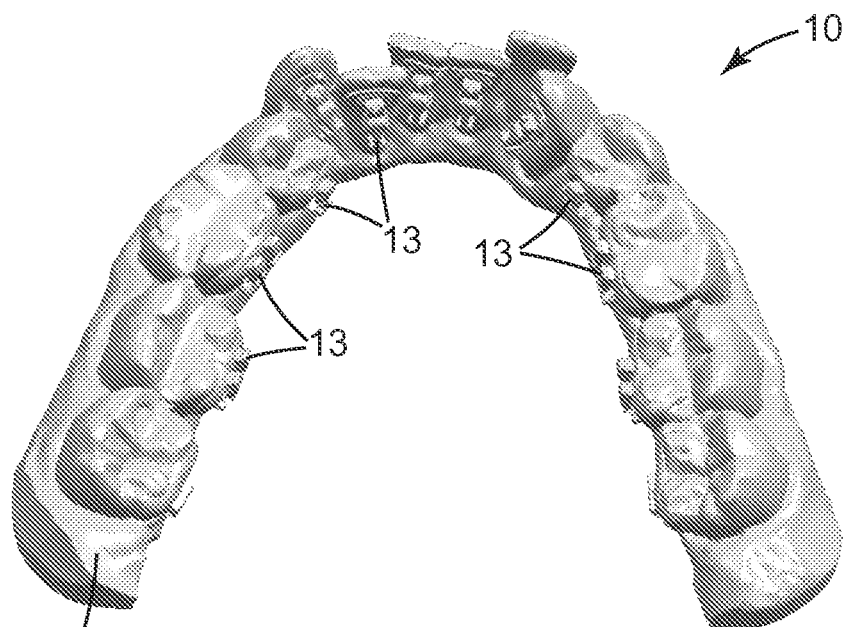
FIG. 3 is a perspective view of a physical mockup according to an embodiment of the disclosure.
Figure 4:
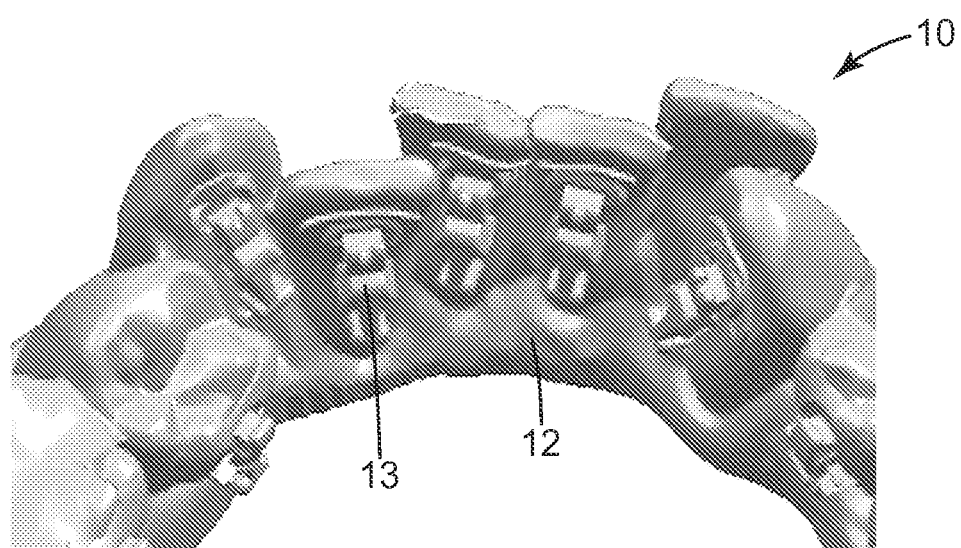
FIG. 4 is a partial enlarged view of FIG. 1

FIG. 3 shows a physical mockup 10 representing a shape composed of the positive shape of a patient's dental arch 12 and the positive shape of a set of analogs 13 (for the sake of clarity not each of the analogs shown is referenced by a reference line in the Figure). The analogs 13 represent or approximate orthodontic brackets as they are used, in combination with an archwire, to move a patient's teeth from a malocclusion toward a desired position. In the physical mockup 10 the patient's teeth are represented in the malocclusion as illustrated in more detail in FIG. 4. Alternatively (though not shown), the physical mockup may include only a portion of the dental arch (for example, an arch quadrant) in instances where a transfer tray is to be used to bond appliances to only a portion of the patient's dental arch.

The physical mockup 10 may be used for physically shaping a transfer tray (not shown in this Figure) for bonding brackets at a predetermined position provided by the transfer tray on a patient's teeth. The transfer tray forms a negative replica of at least part of the physical mockup 10. Such a transfer tray may for example be obtained from taking an impression from the physical mockup 10, from overmolding the physical mockup 10 or from another technique in which the positive physical model 10 is used for, preferably directly, shaping a negative replica. The physical model 10 is preferably configured to provide predetermined undercuts which on the one hand allow orthodontic brackets to be retained or secured within the transfer tray but on the other hand facilitates a removal of the transfer tray from the physical mockup 10 or the patient's teeth without destroying the transfer tray or deboding the bracket from the patient's tooth. Orthodontic brackets often include defined undercuts of a size and shape that could hamper or block a nondestructive removal of the transfer tray, so the brackets are represented in the physical mockup 10 by analog 13 which may not form exact replicas of brackets but just approximate the bracket shape to control undercuts toward a desired level. It is however noted that a bracket which matches with the desired level of undercuts may be represented by an analog forming an exact replica of that bracket, whereas a bracket forming an undesired undercut may be represented by an analog having an approximate shape of such bracket. Accordingly a transfer tray replicated from the physical mockup preferably obtains a shape having the level of undercuts allowing for retaining the brackets and for nondestructive removal of the tray from the patent's teeth.

The physical mockup 10 in the example is manufactured by additive manufacturing, and thus the dental arch 12 and the analog 13 are formed in a single piece in the physical mockup 10. The physical mockup 10 may, in certain circumstances, not be obtained by or consist of an assembly or attachment of the analog 13 onto dental arch 12. Accordingly the position of the analog 13 relative to the dental arch 12 can be determined by computer aid and manual assembly tolerances can be avoided. Examples of suitable additive manufacturing processes include solid freeform fabrication such as 3D printing processes, stereolithography methods, fused deposition modeling, laminated object manufacturing, laser engineered net shaping, selective laser sintering, shape deposition manufacturing, selective laser melting, and solid ground curing. An example of a suitable 3D printing machine is the Eden brand 500V printer from Objet Geometries Ltd., using FullCure 720 acrylic-based photopolymer printing material (also available from Objet Geometries Ltd.).

The manufacturing of the physical mockup in this example is based on a virtual mockup prepared in a computer system. Such a virtual mockup preferably corresponds to a mathematical representation of a three-dimensional shape which can be processed by a computer, for example by a CAD (Computer Aided Design) system. Further the virtual mockup is preferably available in the form of computer data which can be used to control an additive manufacturing machine for manufacturing the physical mockup as defined by the virtual mockup. The virtual mockup may be designed or generated from superimposing or merging a virtual dental arch of a patient with a set of virtual analogs as further described in FIG. 5.

Figure 5:
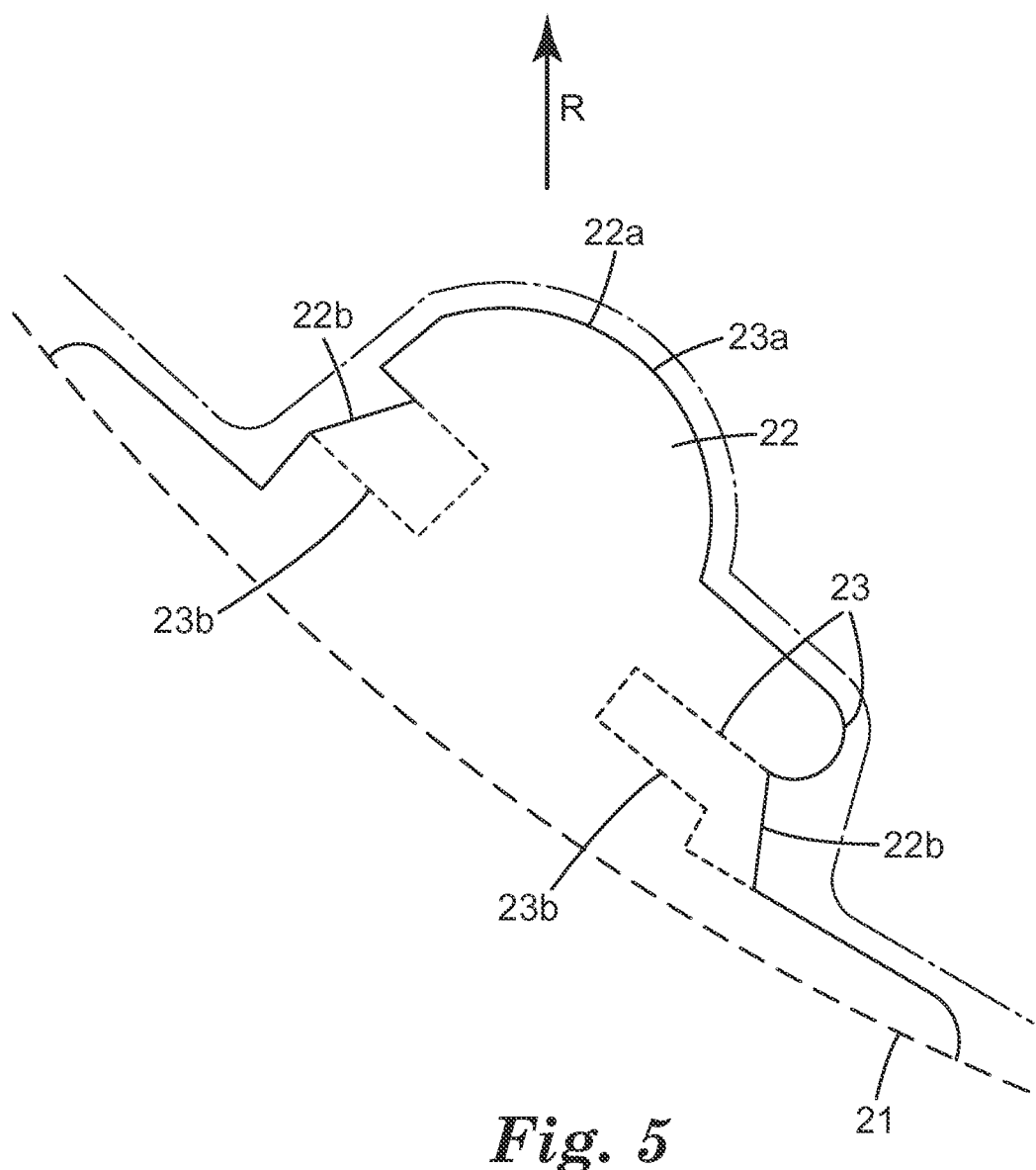
FIG. 5 is a schematic cross-sectional view of a virtual mockup according to an embodiment of the disclosure.

FIG. 5 shows a cross-section of a virtual mockup 20. The virtual mockup 20 combines the shape of virtual analogs (in this view represented by virtual analog 22) and the shape of a virtual dental arch 21. The virtual analog 22 and the virtual dental arch 21 may be obtained from discrete independent virtual parts, or from providing the dental arch 21 and adding the virtual analog 22 to the dental arch 21 by computer aid, for example by additive design or modification of the dental arch 21. The skilled person will be able to use other techniques as known in the field of Computer Aided Design to provide the virtual mockup 10 and to combine the shapes of the virtual analogs and the virtual dental arch.

The shape of a patient's dental arch may be captured by intra-orally scanning at least part of the patient's dentition including the teeth, or by scanning a physical model, for example a plaster model, of the patient's teeth. Scanning devices which allow for providing a virtual dental arch in digital data form are for example available under the designations Lava™ Scan ST and Lava™ Chairside Oral Scanner C.O.S, both from 3M Deutschland GmbH. Alternatively, other intra-oral scanners or intra-oral contact probes may be used, such as the 3M True Definition™ Scanner, available from 3M Company. As another option, the digital data file may be obtained by scanning an impression of the patient's teeth. As still another option, the digital data may be obtained by scanning the physical model of the patient's teeth or by using a contact probe on the patient's teeth. The model used for scanning may be made by pouring a casting material (such as plaster of Paris or epoxy resin) into an impression of the patient's teeth and allowing the casting material to cure. Any suitable scanning technique may be used for scanning the model, such as X-ray, laser, computed tomography (CT), and magnetic resonance imaging.

The digital data may be "cleansed" by removing any data points that represent clear error. For example, files in STL format representing a tooth surface that include a data point significantly outside the normal expected geometrical relationship of adjacent data points could be fixed by STL-handling software to remove the erroneous data point. In addition, tooth data points that are missing could be added by STL-handling software to create realistic, smoothly curved tooth shapes. Alternatively, or in addition to, the data cleansing may be carried out on the data file before conversion of the data to an STL file. As an additional option, data may also be obtained of hidden features of the patient, such as the roots of the patient's teeth and the jaw structure. For example, CT scanning techniques may be used to obtain data representative of the patient's entire tooth structure including the roots. The data obtained by CT scanning may then be "stitched together" with other data obtained by scanning the crowns of the patient's teeth with another scanning technique to provide a more comprehensive virtual representation.

In one embodiment the method further comprises the step of positioning the virtual brackets relative to the virtual dental arch. There are a variety of treatment planning systems which allow for designing and/or placing virtual brackets relative to a virtual dental arch by computer aid. Such systems are, for example, described in U.S. Pat. Nos. 7,210,929, 7,811,087, and 7,993,133. The virtual brackets may be at least partially designed and/or retrieved from a database. Each bracket may be automatically and/or manually positioned relative to a virtual tooth comprised in the virtual dental arch.

In the exemplary implementation, the virtual analog 22 is obtained based on (for example by modification of) a virtual bracket 23. In the exemplary embodiment, the virtual bracket 23 is a lingual bracket, which typically is designed and fabricated individually for every tooth and patient. The person skilled in the art will however recognize that the present methods and systems may likewise be used in combination with labial brackets or a combination of lingual and labial brackets. In one implementation, completely rendered virtual brackets are selected from a library of pre-existing bracket constructions; such bracket constructions may feature a standard or semi-custom bonding pad merged/combined with a bracket body. Such fully-constructed brackets can be stored and accessible as CAD or STL files, for example. The bracket data can be either scanned in using above-described scanning technologies or generated directly with 3D data from published or other profiles.

Another exemplary possibility for providing a virtual bracket with a customized pad is disclosed in U.S. Pat. No. 7,811,087. The bracket design may be performed on a computer that stores a three-dimensional virtual dental arch of a patient. The virtual dental arch may be obtained by scanning the patient's teeth or a physical model of the patent's teeth. Thus the shape of the patient's dental arch, comprising the shape of the teeth and their position relative to each other, can be provided in the form of a computer processable representation (e.g., digital data file). The computer may be equipped with treatment planning or appliance positioning software, which allows for moving the teeth in the virtual model to desired finish positions or placing a bracket at a desired location on the tooth surface, respectively.

An important element of this particular custom bracket is the pad, which provides the surface that enables the bracket to be bonded to a tooth. The tooth facing pad geometry (i.e., bonding surface) may be derived directly from tooth geometries represented in the virtual dental arch so that the pad obtains a three-dimensional surface which substantially exactly matches with the corresponding tooth surface. The term "substantially exactly" in this regard means that the surfaces are identical except for the eventual presence of tolerance deviations that may result from making the pad. This allows for a relatively precise placement of the bracket on the tooth and helps in maximizing the bonding strength.

Another part of the bracket, the bracket body, containing a slot for receiving an archwire and further features (e.g., hooks, tie-wings, grooves, etc.) that allow fastening the wire into the slot, may be available on the computer as predefined virtual models, for example in the form of a library of bracket bodies. To provide a virtual set of brackets for the virtual dental arch certain predefined virtual bodies may be selected. The bracket bodies are typically aligned with their slots relative to each other, for example such that a generally U-shaped virtual archwire can run through the slots of all brackets. Once the slot position of the bracket bodies have been determined the bracket bodies and the respective bracket pads may be combined, for example virtually merged to form the set of virtual brackets. Common CAD programs have capabilities (for example boolean operations) to connect existing shapes to each other. Optionally the design of the virtual brackets, or parts of the brackets, may be adapted to account for a good articulation, hygiene requirements or other aspects as needed.

Next, the virtual brackets are used to generate the set of analogs based thereon. Each analog of the set of analogs is associated with a virtual bracket of the virtual set of brackets, and in certain cases represents a modification thereof. In one embodiment, a modification step comprises increasing a three-dimensional volume represented by the virtual bracket by selectively modifying only a portion of the bracket. For example the modification step may comprise a flattening or reduction of an indentation present in the bracket shape. The modification step may further comprise at least partially filling a space between portions of the bracket shape, or adding a virtual structure to the bracket shape. Thus undercuts which may hinder in the placement of the brackets into the tray or eventually prevent a transfer tray from being removed may be minimized or removed. Further the modification step may comprise optionally reducing the three-dimensional volume by selectively modifying another portion of the bracket. For example the modification step may comprise a rounding of an edge to account for abrasion of a physical bracket during a surface treatment step (for example during deflashing or polishing). Further the modification step may comprise maintaining or substantially of at least a portion of the original virtual bracket shape. Thus the shape of each virtual analog may substantially correspond at least partially to the shape of one virtual bracket of the virtual set of brackets. The person skilled in the art will recognize various possibilities for modifying a shape, for example by change of an existing shape, adding or removing a shape, virtually copying, cutting, extending, reducing or another suitable technique. The skilled person will further be able to create a set of analogs in any suitable manner, for example by functions available on a CAD system, to provide a set of analogs in which the shape of at least one of the analogs differs from the shape of the associated bracket In the example depicted in FIG. 5, the virtual analog 22 and the virtual bracket 23 are associated and have the same shape at first areas 22a, 23a, however differ in shape at second areas 22b, 23b. In particular the second areas 22b of the virtual analog 22 comprise reduced undercuts relative to undercuts present in the second areas 23b of the virtual bracket 23. In the example the undercuts are structures which would (in a physical mockup) retain an imaginary replica 25 against a separation from the virtual mockup 20 in a direction R. Thereby the reduced undercuts in the second areas 22b of the analogs 22 are dimensioned to provide for a lower retention than the undercuts in the second areas 23b of the brackets 23. Accordingly relative to the shape of the bracket 23 the shape of the analog 22 is adapted to facilitate a removal of a transfer tray which is made based on that analog shape. As mentioned one or more of the virtual analogs may substantially exactly correspond in shape to the shape of the virtual bracket, although in most cases the shape of virtual analogs and the shape of the virtual brackets may differ at least in areas comprising undercuts.

The virtual analogs may be provided by virtually replicating the virtual brackets and redesigning of one or more portions of the replicated virtual bracket shape. The computer may have capabilities to determine a virtual retention strength depending on the undercuts present in one more or all of the analogs. For example substantial and/or a high number of undercuts present in a set of analogs may lead to a relatively high virtual retention strength, whereas less substantial and/or a lower number of undercuts may lead to a lower virtual retention strength. Accordingly the computer may be adapted to display a virtual retention strength and optionally upper and lower limits for a desired virtual retention strength to a user. The user may adjust the undercuts of the analogs accordingly by reference to the displayed or calculated virtual retention strength limits. Thus the retention strength of the transfer tray relative to the physical model may be determined during the virtual design, potentially minimizing the need of physically adjusting the physical mockup and/or the transfer tray.

A virtual mockup may be provided by combining the virtual dental arch and the set of virtual analogs, for example being merged or superimposed by computer aid. The virtual mockup, which is preferably present in the form of a computer processable three-dimensional data file may be transmitted to an additive manufacturing machine which manufactures the physical mockup based on the virtual mockup. Alternatively, though not presently preferred, the components of the virtual mockup may be transmitted to the additive manufacturing machine and created separately, with a technician responsible for placement and coupling of the physical analog(s) to the physical dental arch. Such a method may rely on guides or other devices created on the physical arch to assist in analog placement, such as those described in U.S. Pat. Nos. 7,762,815 and 8,235,717. Analogs may be held in place during formation of the placement device, for example, by a temporary adhesive or by friction fit with the guides as described, for example, in U.S. Pat. No. 7,762,815.

Figure 6:
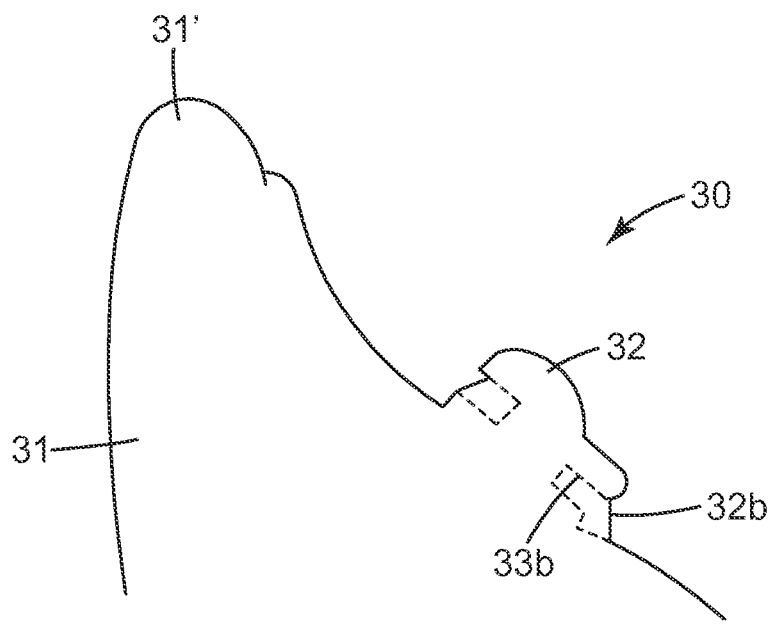

FIG. 6 illustrates a physical mockup 30 having a set of analogs. The physical mockup 30 includes a patient's dental arch 31, which is represented in the Figure by a tooth 31', and a set of analogs, represented in the Figure by analog 32. The analog 32 and the tooth 31' are formed in one piece, and are formed in a contiguous volume of material. Further, although not illustrated in the exemplary figure, the entire set of analogs and the dental arch are formed in one piece. The analog 32 has an undercut area 32b which with respect to an undercut area 33b (illustrated in dotted/dashed lines) of an associated, selected bracket is reduced. It is noted that the physical mockup 30 actually does not include the selected brackets, and a part of a bracket is only provided in the Figure for illustration of the geometric difference between the analog 32 and the associated bracket.

The physical mockup 30 in the example can be made of a light curable material, but may in other examples be made of a plastic material (for example molten from a plastic fiber), metal, gypsum, cement or other chemically hardenable materials.

Figure 7:
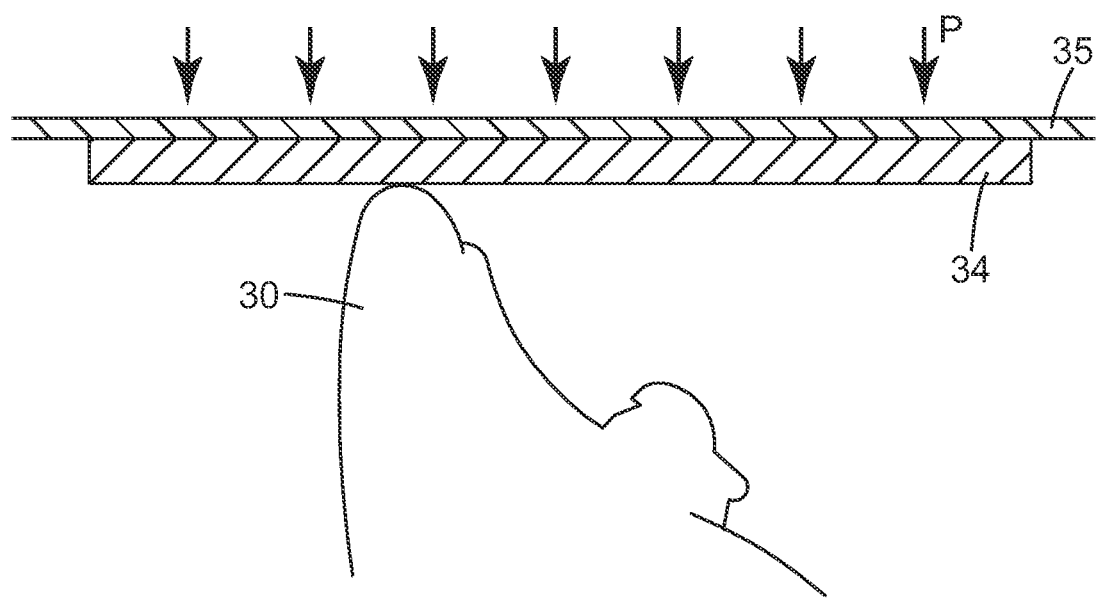
FIGS. 7-11 are schematic cross-sectional views illustrating a method of making a transfer tray according to an embodiment and aspect of the disclosure.
Figure 8:
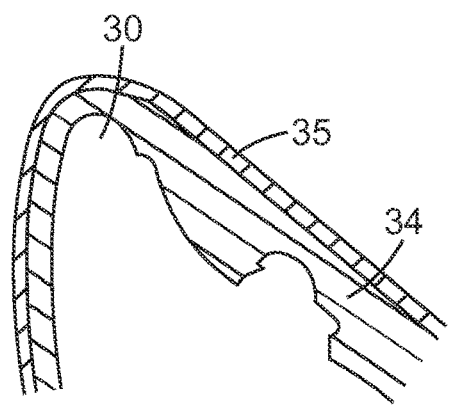

Once the physical mockup is generated to the practitioner's satisfaction, a transfer tray may be created over said mockup. FIG. 7 shows one exemplary method of making a tray, featuring the physical mockup 30 with an elastic sheeting 34 and a plastic sheeting 35 disposed above the occlusal surface of the patient's tooth 31'. The elastic sheeting 34 is placed on top of the occlusal side of the teeth represented by the physical mockup 30, with a plastic sheeting 35 arranged on top of the elastic sheeting 34. The elastic sheeting and the plastic sheeting are deformed, preferably by an air pressure P applied on the elastic and plastic sheeting 34, 35 in directions toward the physical mockup 30. This may be achieved by a vacuum generated beneath the elastic and plastic sheeting 34, 35 or a pressure above the elastic and plastic sheeting 34, 35. At least the plastic sheeting 35 may be heated before and/or during the deformation. As a result the elastic and plastic sheeting 34, 35 are deformed as illustrated in FIG. 8.

The elastic sheeting 34 may be made of a material selected from among dental impression materials, preferably having a shore hardness of about 20 Shore A after hardening, and may have a thickness within a range of about 2 to about 5 mm. The elastic sheeting preferably has a size (or area) that is suitable to embrace the at least part of the labial sides, the occlusal sides and at least part of the lingual sides of the teeth represented in the physical mockup. Further the elastic sheeting 34 may be sized to embrace the entire physical mockup, multiple physical mockups, or portions thereof. Thus the elastic sheeting 34 may have a U-shape along a path which approximately corresponds to the path along which the occlusal sides of the teeth in the mockup are arranged. Alternatively the elastic sheeting 34 may be sized to cover at least a footprint of one or more physical mockups in a plane approximately parallel to the occlusal sides of the teeth in the mockup.

Plastic sheeting 35 is typically plastically, for example thermoplastically, deformable. The plastic sheeting 35 may be made of Duran® polyethylenterephthalate-glycol copolyester, available from Scheu Dental, Germany, and may have a thickness within a range of about 0.5 to about 1.5 mm. Other suitable plastically deformable materials include polycarbonate such as Makrolon brand material from Bayer or Lexan brand material from General Electric. The plastic sheeting 35 may have a size (or area) that corresponds to the size of the elastic sheeting 34, but typically has a larger size.

The plastic sheeting 35 is, in certain implementations, preferably deformable by gas pressure, for example by applying a pressure or vacuum on only one side of the sheeting to cause a pressure difference relative to the other side and thus causing the sheeting to deform over the mockup. The plastic sheeting 35 may be heated before and/or during the deformation process to soften the material the plastic sheeting 35 is made of. Such a so-called thermoforming may be performed using a thermoforming device, for example as available under the designation 508DT from Formech Inc., Chicago, Ill., USA.

Preferably the plastic sheeting 35 is deformed such that it together with the elastic sheeting 34 tightly embraces the teeth represented in the mockup. The elastic sheeting 34 thus acts as a spacing layer causing the plastic sheeting 35 to form around the teeth at a certain distance determined by the thickness of the elastic sheeting 34.

FIG. 8 shows the physical mockup 30 embraced by the elastic sheeting 34 and the plastic sheeting 35. The plastic sheeting 35 is preferably a clear thermoplastic film which conforms to the outer surface of the elastic sheeting 34. The plastic sheeting 35 is preferably allowed to solidify by cooling so as to provide it with a sufficient rigidity for handling. As illustrated the elastic sheeting 34 spaces the plastic sheeting 35 from the physical mockup 30.

In another example (not shown) instead of an elastic sheeting a space coat may be used. Such a space coat may be obtained from applying a hardenable liquid or pasty material over the physical mockup 30, and allowing the material to solidify. This may be performed by dip coating, or manual coating using a dispensing syringe or brush. In the solidified state the coating material is preferably elastic or brittle such that it can be removed from the physical mockup at a later stage. A plastic sheeting may be deformed over the coated mockup as described above.

In still a further example a space coat may be applied in an additive manufacturing machine along with the build-up of the physical model. In such a build-up process a relatively hard and a relatively soft material may be printed in three dimensions, with the hard material forming the physical mockup and the soft material forming the space coat. The soft material may be a so-called support material, which is typically used for layer-wise vertical printing of vertically spaced structures and removed after printing. An additive manufacturing machine which provides for such a printing process is for example available under the designation Projet™ Series from the company 3D systems, USA.

Figure 9:
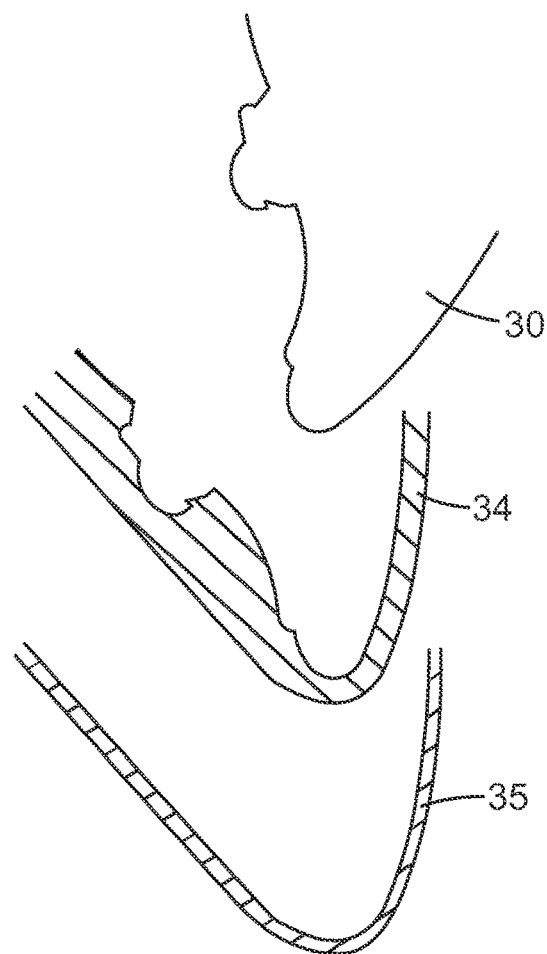

Next, the plastic sheeting, if thermoformed, can be allowed to cool, thereby obtaining a sufficient stiffness for handling. The plastic sheeting and the elastic sheeting may be removed from the physical mockup, and the elastic sheeting may be removed from the plastic sheeting. FIG. 9 illustrates a separation of the elastic sheeting 24 from the physical mockup 30 and the plastic sheeting 35. The elastic sheeting 34 may be disposed and the physical mockup 30 and the plastic sheeting 35 may be used to form the transfer tray for the corresponding physical brackets.

The plastic sheeting, after deformation, may have a generally trough-shaped indentation or cavity which approximates a three-dimensionally proportionally enlarged shape of the teeth (including the analogs) represented in the physical mockup. The indentation may be filled with a hardenable material as further described below with respect to FIG. 8. Exemplary hardenable materials include: Kanisil®, a silicon carbide containing alloy (available from Heinrich Schnarr GmbH, Germany); Odontosil™, an addition-vulcanising silicone available from Dreve Dentamid GmbH, Germany; and Memosil 2 brand vinyl polysiloxane material from Heraeus Kulzer Inc. In certain implementations, the mockup may be mated with the deformed plastic sheeting so as to enclose the hardenable material between the mockup and the sheeting. The amount of the hardenable material is preferably selected such that during mating of the mockup and the sheeting the hardenable material flows around (typically to embed relevant parts of) the teeth and analogs represented in the mockup. The mated mockup, hardenable material and sheeting may be exposed to a vacuum or pressure, for example by use of an autoclave or pressure chamber, in order to minimize voids or bubbles between the teeth and the hardenable material. The hardenable material may subsequently be allowed to harden or may be cured. The hardened flowable material is preferably elastic and has a shore hardness of between about 50 shore A and 70 shore A, preferably about 60 Shore A. The hardened flowable material and the deformed plastic sheeting cooperate to form the transfer tray.

The mockup and the transfer tray in a situation mated with each other preferably define one or more a reference axes along a direction in which the transfer tray is at least partially removable from the mockup. Different sections (for example a section of one tooth) of the mockup and the transfer tray may define different (or slightly different reference axes) however in the following it is referred to one reference axis only for the sake of simplicity. The modification of the shape of one or more of the brackets preferably comprises a reduction or elimination of an undercut formed by at least one of the brackets and suitable to lock or retain the transfer tray against a movement along the reference axis. In other words relative to a bracket shape the associated analog shape may provide a lower retention of the transfer tray mated on the physical mockup.

In one embodiment the transfer tray replicates the negative shape of only part of the physical mockup, for example the shape of only one analog and the shape of at least part of a tooth in the dental arch. A partial transfer tray may for example allow for rebonding or replacing a bracket in a patient's mouth. The mockup may be adapted such that the transfer tray obtains one or more separation markers at predetermined positions. A user of the transfer tray may separate (for example cut) the tray at a separation marker and thus obtain a partial transfer tray. The mockup may therefore be provided such that it comprises one or more bulges or ridges which replicate corresponding recesses or notches in the tray. Instead or in addition to a separation marker a position marker may be provided on the mockup in the form of a raised or recessed structure, such as for example a position marker indicating the center of a tooth. Further the mockup may be provided such that it comprises raised or recessed numbers which indicate the tooth number and/or the quadrant number.

Figure 10:
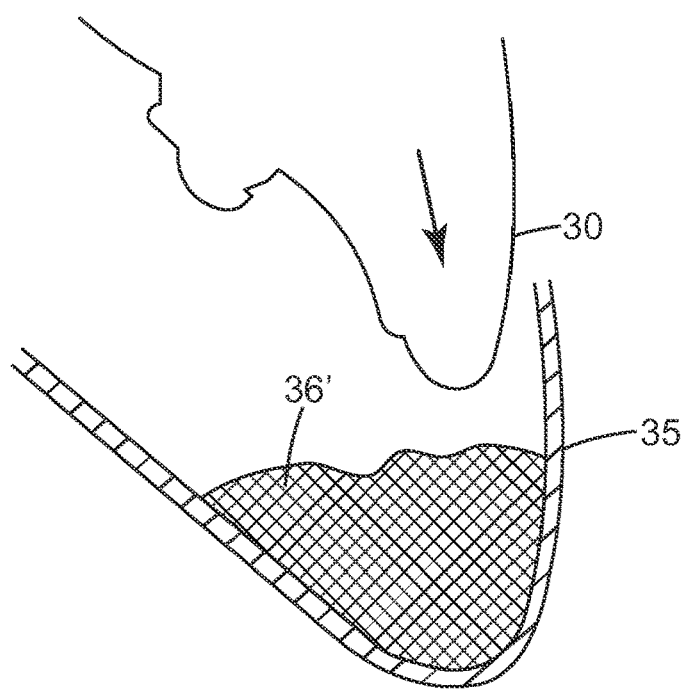
Figure 11:
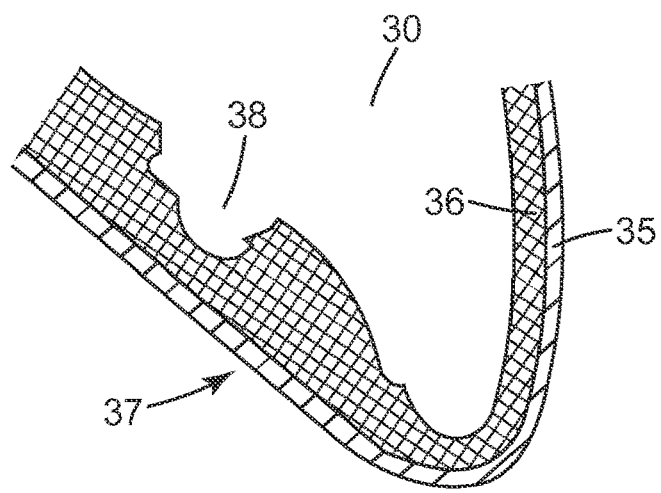

FIG. 10 shows the plastic sheeting 35 having a cavity formed by the coated physical mockup as described above. A typically clear, hardenable material 36' is received within the cavity of the plastic sheeting 35. The physical mockup 30 can be mated with the plastic sheeting 35 and thereby dipped into the hardenable material 36' which thereby preferably distributes between the outer surface of the physical mockup and the inner surface of the cavity as shown in FIG. 11. Optionally the combined physical mockup 30, the hardenable material 36' and the plastic sheeting 35 are exposed to an increased pressure relative to the normal atmospheric pressure to minimize voids or bubbles in the hardenable material 36', in particular between the outer surface of the physical mockup 30 and the inner surface of the hardenable material 36'. The hardenable material 36' is allowed to harden to provide a positioning layer 36 for the brackets. Under this particular method, the positioning layer 36 in combination with the plastic sheeting 35 forms the transfer tray 37. Under presently preferred circumstances, the positioning layer 36 is adapted such that it can position and retain the bracket and further such that it is deformable for receiving brackets therein and removing brackets therefrom. Accordingly the positioning layer 36 may be made of a relatively elastic and soft material (when solidified). Therefore the transfer tray 37 comprises the plastic sheeting 35 which preferably provides the tray with the required mechanical stiffness and stability, and the positioning layer 36 which preferably provides the transfer tray with a series of receptacles in which the bracket can be precisely and removably retained. The positioning layer 36 approximately corresponds in shape with the shape of the elastic sheeting described above, however is typically made of a different material.

Optionally, the transfer tray may be created having an occlusal stop member, as described in U.S. Pat. No. 7,845, 938. An occlusal stop member typically includes a flat top surface and a bottom surface with shapes such as recesses that match the shapes of the occlusal tips of the patient's dental arch. In certain implementations, the occlusal stop member has a recess or recesses corresponding to only some of the teeth in the dental arch, although it is also possible to construct an occlusal stop member that has one or more recesses corresponding to each tooth of the dental arch. Other variations are also possible. For example, the occlusal stop member may extend only along a portion of the dental arch instead of along the entire dental arch. A plurality of stop members may be provided, potentially spaced apart from each other and optionally connected together. The occlusal stop member may be chemically or mechanically bonded to the plastic sheeting and/or the hardenable material.

It should be appreciated that the transfer tray may be formed only of one or more layers of deformable plastic sheeting, without accompanying elastic sheeting or positioning layer. In such implementations, the plastic sheeting may be disposed directly proximate the occlusal surface of the physical mockup, without the spacing provided by elastic sheeting. The plastic sheeting accordingly directly embraces the teeth and bracket analogs of the physical mockup upon deformation, directly creating the bracket receptacles used to removably retain brackets for subsequent bonding. In such streamlined transfer tray embodiments, the physical mock up may be coated with a release agent to assist in removal of the transfer tray from the mockup. Pursuant to typical methods used to create the transfer tray, the resulting tray represents a negative replica of at least a portion of the physical mockup.

As another alternative (not depicted in the Figures), a virtual transfer tray may be directly derived from the virtual mockup, using methods described in US Publication No. 2011/0091832. In one exemplar of such a method, the derivation can proceed by defining a guidance line that extends across at least a portion of the arch and is spaced away from the arch and mounted analogs. For example, the guidance line follows a curved path that is generally parallel to the facial surfaces of the virtual analogs and generally lies in an occlusal plane. In one computer-assisted embodiment, the guidance lines are defined by tracing a line segment that connects the facial-most edges of analogs as viewed from the occlusal direction, offsetting the line segment outwardly towards the facial direction by a certain distance and then applying a smoothing operation to the line segment. If desired, the certain distance can be used to define a desired tray thickness. The process may continue by defining a series of fitted arcs, each of which extends over the lingual, occlusal, and facial surfaces of the virtual arch model and intersects each guidance line in a generally perpendicular relationship such that each fitted arc passes over, without contacting, the virtual model and virtual analogs.

An exterior surface of the virtual transfer tray may be formed by fitting a surface to the set of fitted arcs. In some embodiments, the exterior surface is an open-ended shell that completely covers the occlusal, lingual, and facial sides of the virtual mockup that includes the model and analogs. Optionally, a surface smoothing operation is subsequently executed on the exterior surface. Then the remainder of a virtual tray body is derived using the exterior surface. The solid virtual tray body may be formed by defining a composite surface that includes the exterior surface and a planar surface that extends across the cavity formed by the exterior surface. When virtually aligned with the virtual mockup, the virtual tray body surrounds both the teeth and analogs. The mockup (including analogs) may then be virtually subtracted from the virtual transfer tray body to produce a virtual tray precursor. Virtual tray precursor includes a tray body which will typically have a shell-like configuration and further includes one or more receptacles formed by the negative virtual imprints of the analogs. The virtual tray precursor, which is preferably present in the form of a computer processable three-dimensional data file may be transmitted to an additive manufacturing machine which manufactures the physical transfer tray based on the virtual tray precursor according to techniques discussed above.

Regardless of the method of physical tray creation, the positioning layer 36 and/or the plastic sheeting 35 may be trimmed in size to match with only a part of a patient's dental arch or to make the tray fit conveniently in a patient's mouth.

Figure 12:
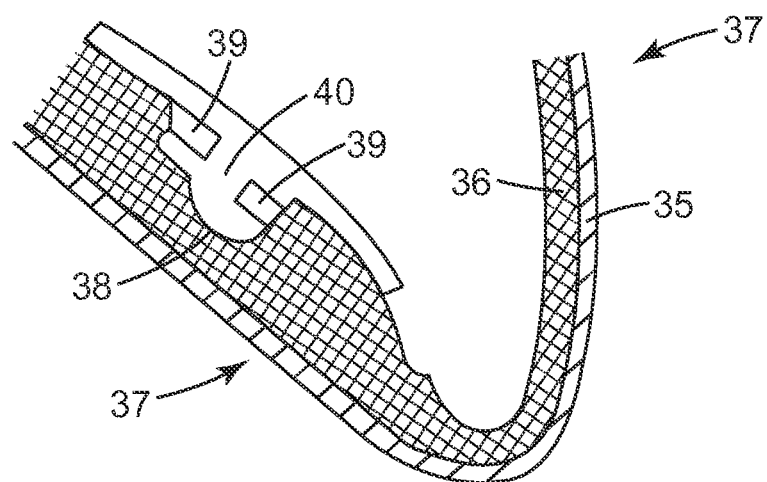
FIG. 12 is a schematic cross-sectional view of a bracket being placed into a transfer tray according to an embodiment of the present disclosure.
Figure 13:
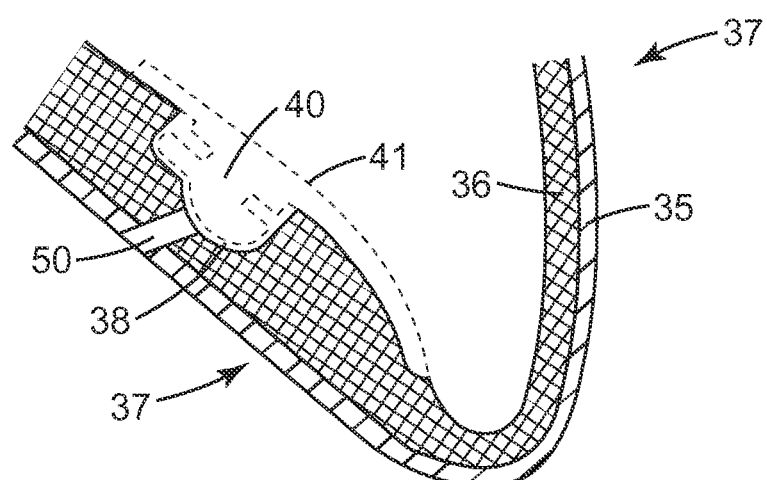
FIG. 13 is a schematic cross-sectional view of a transfer tray featuring a channel for introduction of filler material.

As illustrated in FIGS. 11-13, the formed tray includes a series of receptacles (represented by receptacles 38) that substantially correspond to exterior surfaces of a bracket analog. Typically, the tray will include a receptacle corresponding to each bracket analog on the physical mockup. In circumstances wherein the analog includes a modified undercut relative to the corresponding bracket, the placement of the actual physical bracket in the receptacle 38 creates one or more voids 39 between the bracket body 40 and receptacle surfaces 38a. In addition, defects or tolerable deviations introduced during bracket manufacturing can result in additional voids 39 between the bracket body 40 and a receptacle wall. Excess adhesive on the base of the bracket can flow into or otherwise fill these voids 39 during placement of the bracket on a tooth surface. The adhesive typically demonstrates an affinity for bracket surfaces and is difficult to remove once engaged, deleteriously affecting the bracket function as described above.

Under the methods of the present disclosure, a filler material can be introduced into a tray receptacle to protect the voids 39 from excess adhesive while the bracket is bonded to a tooth. In presently preferred circumstances, the filler is a volume constant material; in that it does not lose appreciable volume once it is cured or hardened. Particularly useful volume constant materials include the flowable, hardenable materials used to create positioning layer 26, such as Odontosil™. Suitable volume constant materials also include wax and other dental impression materials. In other embodiments, the filler material may be expandable foam, which is introduced at a lesser volume and subsequently expanded to fill one or more voids. Materials used for the expandable foam includes polyethylene, polyurethane, silicone, or synthetic rubbers, such as ethylene-propylene diene or block copolymers, such as those based on styrene. If desired, a filler material such as polyvinyl acetate, which does not typically exhibit volume constant behavior may be used. In such implementations, however, the filler may fill less than the full extent of the voids, leaving additional, smaller voids and crevices susceptible to excess adhesive.

The filler is introduced into the receptacle at a volume effective to fill or otherwise protect the voids 42, which is typically no greater than 0.1 ml for an entire series of receptacles on a patient's arch.

In presently preferred circumstances, the filler is at least initially flowable and is introduced into a receptacle via a channel or other passage. Typically, the filler is introduced after a bracket has been placed in the receptacle. The filler can be injected through the channel and allowed to flow into the cavities and voids, where it is then cured or otherwise hardened in place. In other implementations, the filler may be coated or coupled to the tray prior to introduction of the bracket into the receptacle. In yet other implementations, the bracket body may be coated with a filler material prior to being seated in the receptacle. For example, at least the archwire slot and undercuts may be coated or dipped in wax before each bracket of the bracket set is placed in the corresponding receptacle. Excess wax may then be removed using common techniques to prevent a bracket misfit within the receptacle.

If the filler is to be introduced after the bracket has been coupled to the tray, a channel 50 may be formed through the tray (including position layer 36 and sheeting 35) to provide access to the receptacle 38. FIG. 13 depicts a channel 50 provided proximate a representative receptacle 38. In presently preferred circumstances, a channel is formed proximate each receptacle created in the transfer tray. In one implementation, the channel 50 is formed through use of a piercing tool, drill, or other bore to penetrate both the plastic sheeting and the positioning layer. In another implementation, the exterior, plastic sheeting may be removed, with the channel formed in the positioning layer. In yet other implementations, the channel 50 may be formed by piercing the positioning layer first and boring through the plastic sheeting to the exterior of the tray. Alternatively, the channel 50 may be made by causing a post-like structure to protrude from the bracket body before taking the steps described above to create the transfer tray.

The channel 50 is typically, substantially cylindrical and typically features a diameter of at least 1.0 mm and no greater than 1.5 mm to provide adequate flow of the filler into the receptacle. In other implementations (not shown), the exterior opening 52 of the channel 50 may feature a conical or frustoconical shape, providing a funnel into the receptacle 40 and/or portions of the channel 50. To enhance effective filling of voids, the channel 50 extends from an exterior surface of the transfer tray opposite the receptacle through the each layer of tray material. The channel 50 typically engages receptacle 40 at or near the position of the center of the bracket body (shown in outline form). In use, the filler is thus initially introduced relative to a bracket surface opposite or remote from the bonding base. For the lingual bracket placement embodiment depicted in the Figures, the channel 50 is formed through an opening on the lingual surface 39 of the tray. For a transfer tray used to place one or more brackets on labial tooth surfaces, the channel 50 will include an opening on the facial, exterior surface of the tray. Designing the channel to include an opening on the exterior surface of the tray allows for the filler to be introduced after the bracket is placed in the receptacle, which can potentially ease tray handling and manufacturability.

Figure 14:
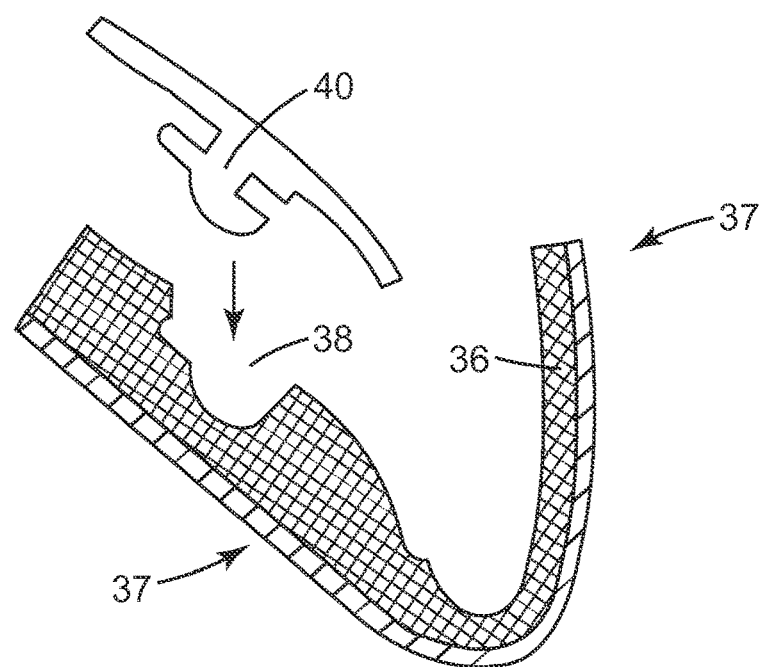
FIG. 14 is a schematic cross-sectional view of a transfer tray having a bracket placed in a receptacle, according to an embodiment of the disclosure.

To utilize the transfer tray 37 as illustrated in FIG. 14 brackets (represented by bracket 40) are placed in associated receptacles (represented by receptacle 38) in the positioning layer 36. A thin layer of a release agent may be applied to the transfer tray 37 and allowed to dry. An example of a suitable release agent is a water soluble polyvinyl alcohol, such as "PA0810" from PTM & W Company of Santa Fe Springs, Calif. Other suitable release agents include silicone fluids, sprays, and wax emulsions. Use of a release agent can ease the removal of the bracket from the receptacle and, if desired, the filler from tray. The ability to remove the filler material from the tray particularly enhances the use of a tray for rebonding purposes.

Placement of the bracket in the receptacle may be performed bracket by bracket manually or by picking up a set of brackets pre-placed on a physical model of the patient's teeth, in that the empty transfer tray (without the brackets) can be mated with the physical model of the patient's teeth including the brackets and by separating the transfer tray from the model of the patient's teeth. In the latter step the brackets preferably are retained in the transfer tray and released from the model. This may be achieved by a relatively slight temporary bond (e.g., by temporary or weak adhesive) between the brackets and the model.

Figure 15:
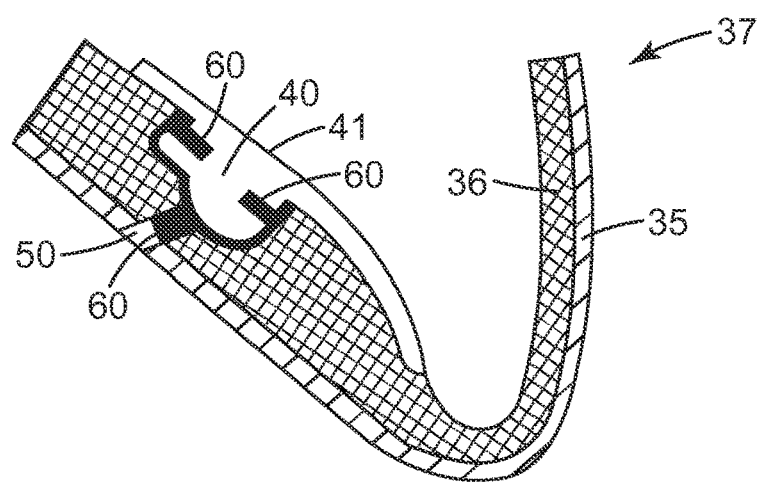
FIG. 15 is a schematic cross-sectional view of a transfer tray and bracket assembly after a filler material has been introduced into a receptacle, according to an embodiment of the disclosure.

Once the bracket is seated in the receptacle, the filler may be introduced through the channel and allowed to flow into the voids, where it is then cured or otherwise hardened in place. In embodiments featuring a channel through only the positioning layer, the plastic sheeting can be returned to the tray body after the filler is introduced and/or hardened. Of course, if the filler is coated or otherwise disposed on the bracket itself, the introduction of the filler will be simultaneous with the seating of the bracket. FIGS. 14 and 15 depict the introduction of a filler material 60 through channel 50 proximate a representative receptacle 38. The filler material 60 as illustrated enters the voids 39 now defined in the receptacle 38 and is subsequently allowed to harden. Hardening may be effectuated through use of, for example, ultraviolet light, heat, or time. If the filler material comprises wax, it is typically introduced into the channel 50 and receptacle 38 at elevated temperatures; accordingly, the wax composition is allowed to cool in order to harden.

An adhesive may be applied to the pad surface 41 of the bracket 40 (and further brackets present in the tray) and the transfer tray may be placed on the teeth in a patient's mouth where the adhesive is caused or allowed to harden to establish a bond between the brackets in the tray and the patient's teeth. Once the bond is established the plastic sheeting 35 may be removed, thereby leaving the positioning layer 36 in place on the patient's teeth. The positioning layer 36, due to its elastic properties and no longer supported by the plastic sheeting 35, can thus be easily peeled off from the patient's teeth and the brackets bonded thereon. As shown in the FIG. 15, the spaces between the positioning layer 36 and the bracket 40 are occupied with the separate filler material 60 in undercut areas of the bracket 40, thus not substantially interfering with the separation between the positioning layer 36 and the bracket 40. Accordingly forces on the brackets bonded to the patent's teeth, and thereby the risks of breaking or affecting the bonds during removal of the transfer tray are minimized.

Due to the use of clear materials for the positioning layer 36 and the plastic sheeting 35 proper placement of the transfer tray 37 on a patient's teeth is facilitated. Further the clear material allows for visually determining a proper positioning of the brackets within the transfer tray.

Additionally, the transfer tray 37 may be used for bonding only a single appliance to a patient's tooth. For example, a portion of the transfer apparatus described above may be used to bond a single appliance to a single tooth subsequent to the time that other appliances are bonded, such as in instances where access to the tooth is initially hindered by other teeth. As another example, a portion of the transfer apparatus described above may be used to re-bond one or more appliances that have unintentionally debonded from the tooth, or to bond a new appliance to a tooth to replace the original appliance. In such instances, it may be desirable to remove any remaining filler material from the tray.

The complete disclosures of the patents, patent documents, and publications cited herein are incorporated by reference in their entirety as if each were individually incorporated. A number of other variations, modifications and additions are also possible without departing from the spirit of the invention. Accordingly, the invention should not be deemed limited to the specific embodiments described above, but instead only by a fair scope of the claims that follow and their equivalents.

The invention claimed is:

1. A method of making a transfer tray, comprising the steps of:
   providing a physical mockup having a shape that corresponds to a positive shape of a patient's dental arch and a positive shape of one or more bracket analogs;
   forming a transfer tray over the physical mockup, the transfer tray comprising a negative replica of at least a portion of the mockup, wherein forming the transfer tray creates one or more receptacles, each receptacle featuring a least a portion of the shape of a bracket analog;
   forming a channel in the tray proximate each receptacle, wherein the channel extends from an exterior surface of the tray to the receptacle;
   placing a bracket associated with a bracket analog into a receptacle of the one or more receptacles, wherein the bracket includes a bonding base and a surface opposite the bonding base; and
   introducing a filler material into at least one receptacle through the channel to the surface opposite from the bonding base, wherein a receptacle and the associated bracket define one or more voids when the associated bracket is placed in the receptacle, and wherein the filler material fills at least one void.

2. The method of claim 1, wherein forming the tray comprises:
   providing an elastic sheeting on the physical mockup to cover at least part of the tooth side of the mockup by the sheeting;
   providing a plastic sheeting on the mockup with the elastic sheeting arranged between the plastic sheeting and the mockup;
   deforming the plastic sheeting over the mockup such that it encloses at least the tooth side of the mockup and such that it embraces the elastic sheeting between the plastic sheeting and the mockup;
   replacing the elastic sheeting with a hardenable material; and
   allowing the hardenable material to harden.

3. The method of claim 1, wherein the shape of each analog approximates or represents the shape of the associated bracket; and wherein at least one of the analogs has a different shape than the associated bracket.

4. The method of claim 1, wherein the bracket analog includes less substantial or fewer undercuts or recesses than the associated bracket body.

5. The method of claim 4, wherein the filler material comprises a hardenable material, and wherein the method further comprises allowing the hardenable material to harden.

6. The method of claim 1, wherein the filler material is introduced after the associated bracket has been placed in the receptacle.

7. The method of claim 1, wherein the filler material is introduced simultaneously with the placement of the associated bracket in the receptacle.

8. The method of claim 1, wherein the filler material is selected from the group consisting of silicone and wax.

9. The method of claim 1, wherein providing the physical mockup comprises the steps of:
   providing a virtual dental arch replicating at least part of the patient's dental arch;
   providing a virtual set of orthodontic brackets for the virtual dental arch;
   providing a virtual set of analogs, each analog being associated with a virtual bracket of the virtual set of brackets, wherein each of the virtual analogs approximates or represents the shape of the associated virtual bracket, wherein the shape of at least one of the analogs differs from the shape of the associated bracket;
   providing a virtual mockup wherein the virtual dental arch and the set of virtual analogs are merged; and
   manufacturing the physical mockup based on the virtual mockup.

10. The method of claim 9, further comprising the step of modifying the shape of at least one virtual bracket to form at least one of the virtual analogs.

\* \* \* \* \*

UNITED STATES PATENT AND TRADEMARK OFFICE
CERTIFICATE OF CORRECTION

PATENT NO. : 10,368,961 B2
APPLICATION NO. : 15/105484
DATED : August 6, 2019
INVENTOR(S) : Ralf Paehl It is certified that error appears in the above-identified patent and that said Letters Patent is hereby corrected as shown below:

On the Title Page

Abstract:
Column 2, Line 8, delete "a least" and insert -- at least --

In the Specification

Column 3, Line 59, delete "a least" and insert -- at least --

Column 5, Line 40, delete "1" and insert -- 1; --

Column 6, Line 36, delete "deboding" and insert -- debonding --

Column 9, Line 45, delete "bracket" and insert -- bracket. --

Column 11, Line 27, delete "polyethylenterephthalate" and insert -- "polyethyleneterephthalate --

In the Claims

Column 18, Line 3, delete "a least" and insert -- at least --

Signed and Sealed this
Twenty-second Day of June, 2021

Drew Hirshfeld
*Performing the Functions and Duties of the
Under Secretary of Commerce for Intellectual Property and
Director of the United States Patent and Trademark Office*